United States Patent [19]

Dankowski

[11] Patent Number: 4,959,497

[45] Date of Patent: Sep. 25, 1990

[54] PROCESS FOR THE PRODUCTION OF WATER INSOLUBLE PEROXYCARBOXYLIC ACIDS

[75] Inventor: Manfred Dankowski, Karlstein, Fed. Rep. of Germany

[73] Assignee: Degussa Akteingesellschaft, Frankfurt am Main, Fed. Rep. of Germany

[21] Appl. No.: 344,483

[22] Filed: Apr. 27, 1989

Related U.S. Application Data

[63] Continuation of Ser. No. 688,359, Jan. 2, 1985, abandoned.

[30] Foreign Application Priority Data

May 18, 1984 [DE] Fed. Rep. of Germany ....... 3418450

[51] Int. Cl.$^5$ ............................................ C07C 409/00
[52] U.S. Cl. ........................................ 562/006; 562/3; 252/321
[58] Field of Search .................... 260/502 R; 252/321; 562/6, 3

[56] References Cited

U.S. PATENT DOCUMENTS

| | | | |
|---|---|---|---|
| 2,624,655 | 1/1953 | Greenspan ...................... | 260/502 R |
| 2,663,621 | 12/1953 | Greenspan et al. ................. | 423/265 |
| 3,956,159 | 5/1976 | Jones .................... | 252/104 |
| 4,119,660 | 10/1978 | Hutchins ......................... | 260/502 R |
| 4,370,251 | 1/1983 | Liao et al. ....................... | 260/502 R |

FOREIGN PATENT DOCUMENTS

| | | | |
|---|---|---|---|
| 630363 | 7/1963 | Belgium .......................... | 260/502 R |
| 45290 | 2/1982 | European Pat. Off. ......... | 260/502 R |
| 117580 | 7/1958 | U.S.S.R. ......................... | 260/502 R |
| 2032421 | 5/1980 | United Kingdom ............ | 260/502 R |

OTHER PUBLICATIONS

Translation of USSR Inventor's Certificate No. 117,580; Inventor P. S. Ugryumov; application date: 7/10/58.

Parker et al, *J. Am. Chem. Soc.*, vol 79, pp. 1929–1931, (1957).

Ugryumov, *Chemical Abstracts*, vol. 53, No. 19980i, (1959).

Greenspan et al II, *Chemical Abstracts*, vol. 50, No. 2932f, (1956).

*Primary Examiner*—Bruce Gray
*Attorney, Agent, or Firm*—Cushman, Darby & Cushman

[57] ABSTRACT

The invention is directed to a process for hte production of water insoluble peroxycarboxylic acids in which the carboxylic acid is suspended in the reaction mixture and reacted with hydrogen peroxide in the presence of pyridine-2,6-dicarboxylic acid.

5 Claims, No Drawings

PROCESS FOR THE PRODUCTION OF WATER INSOLUBLE PEROXYCARBOXYLIC ACIDS

This is a continuation of Ser. No. 07/688,359, filed Jan. 2, 1985, which was abandoned upon the filing hereof.

BACKGROUND OF THE INVENTION

The invention is directed to a process for the production of water insoluble peroxycarboxylic acids.

These types of compounds are not only employed as oxidation agents in organic syntheses but also in the washing or bleaching of textiles since their action occurs even at temperatures below 80° C.

There have already been published a number of different processes for the production of water insolube peroxycarboxylic acids.

European published application A-2-0045290 is directed to a process for the production of peroxycarboxylic acids in which the starting carboxylic acids are dissolved in concentrated sulfuric acid and the peracids formed by oxidation with hydrogen peroxide are continuously extracted with an organic solvent.

Likewise, in U.S. Pat. No. 4,119,660, there is described a process in which the starting carboxylic acids are dissolved in a large excess of sulfuric acid and are subsequently reacted to form the perocarboxylic acids.

In this process the sulfuric acid acts as catalyst and solvent for the starting carboxylic acid.

Since the catalytic action, however, even occurs at small concentrations, the use of these amount is also possible in the known process.

It has been found, however, that in this case in the production of water insoluble peroxycarboxylic acids having at least 6 carbon atoms there occurs strong foam formation if the starting carboxylic acid is not present in dissolved form in the reaction mixture but instead forms a suspension.

The problem of the invention was to develop a process for the production of peroxycarboxylic acids having at least 6 carbon atoms in which there is suppressed the formation of foam.

SUMMARY OF THE INVENTION

The subject matter of the invention is a process for the production of water insoluble peroxycarboxylic acids by reaction of an aliphatic carboxylic acid having 6 to 16 carbon atoms or an aromatic containing hydrogen peroxide, water, and sulfuric acid in which the respective carboxylic acid is suspended in the oxidation mixture and the reaction is carried out in the presence of 0.01 to 10 wt. %, preferably 0.25 to 1.6 wt. % of

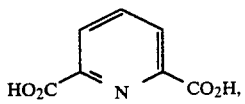

pyridine-2,6-dicarboxylic acid (PDCA), based on the hydrogen peroxide employed.

Examples of aliphatic carboxylic acids include alkanoic acids such as hexanoic acid, heptanoic acid, octanoic acid, nonanoic acid, decanoic acid, dodecanoic acid, tetradecanoic acid, and hexadecanoic acid, alkanedioic acids such as adipic acid, pimelic acid, suberic acid, azelaic acid, sebacic acid, dodedcanedioic acid, brassylic acid, tetradecanedioic acid, and hexadecanedioic acid. Examples of aromatic carboxylic acids include benzene monocarboxylic acids such as benzoic acid, toluic acid, e.g. p-toluic acid, p-ethylbenzoic acid, and benzenedicarboxylic acids such as phthalic acid, isophthalic acid, and terephthalic acid.

The reaction is carried out with a molar ratio of hydrogen peroxide to carboxylic acid of 1 to 10:1, preferably 1.5 to 3:1.

Especially suitable are aliphatic mono and dicarboxylic acids having a total of 9 to 13 carbon atoms and among these there are preferred dicarboxylic acids of the formula

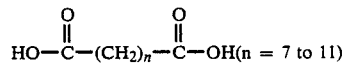

especially azealic acid, dodecanedoic acid and brassylic acid. As aromatic acids there are preferred phthalic acid and its isomers.

In carrying out the process of the invention it has been found favorable to employ sulfuric acid and carboxylic acid in the molar ratio of 1 to 10:1, preferably 2 to 4:1. In general, it is essential in selecting the molar ratios that the starting carboxylic acid form a suspension in the respective oxidation mixtures.

Furthermore, it has been found that the best results are obtained if the PDCA is dissolved in a mixture of water containing hydrogen peroxide and sulfuric acid and then the carboxylic acid is suspended in this mixture.

The reaction is carried out at a temperature between 35°-70° C., preferably 35°-60° C.

Hydrogen peroxide is employed in a concentration of 30 to 99 wt. %, preferably 40 to 50 wt. %, sulfuric acid in a concentration of 20 to 98 wt. %, preferably 90 to 98 wt. %.

The use of PDCA in the oxidation mixture should not be confused with the known employment of this compound for the stabilization of peroxycarboxylic acid preparations (U.S. Pat. No. 3,956,159).

By proceeding according to the invention, the production of peroxycarboxylic acids having at least 6 carbon atoms to form an oxidation mixture containing suspended carboxylic acid is made possible industrially since, in contrast to earlier procedures, the formation of foam is suppressed to such an extent that there are obtained handleable, i.e., for example pumpable, mixtures.

The formation of foams made of very fine gas bubbles in the entire mixture which occurs without the addition of PDCA, however, not only creates problems in carrying out the process industrially, but also influences the reaction, since the wetting of the suspended caraboxylic acids with the oxidation mixture is prevented by the clinging gas bubbles.

The reaction product is separated from the reaction mixture in the usual manner by filtering or centrifuging and dried. If pure peroxycarboxylic acid is to be recovered without additional phlegmatizing salts, then the product must be washed free of mineral acids.

The peroxycarboxylic acids are stabilized outstandingly if before, during or after the reaction. There is added to the oxidation mixture a phlegmatization agent.

There can be used as such phlegmatization agents for example, alkali metal, magnesium, alkaline earth metal, or earth metal sulfates or boric acid. Thus there can be used as sulfates, for example, sodium sulfate, potassium sulfate, magnesium sulfate, calcium sulfate, or barium sulfate.

These materials can be used either in solid form or as aqueous solutions or suspensions. It is also possible to produce them in situ before or during the reaction and/or in the suspended product before its separation from the reaction solution.

There is especially suited for this purpose a process in which the reaction of water insoluble carboxylic acid with the oxidation mixture is carried out in the presence of PDCA at 45°-60° C., thereupon the reaction mixture is cooled to 45° to 5° C., preferably 40° to 32° C., an aqueous alkali sulfate solution added, the pH of the mixture adjusted to 2-6, preferably 3 to 4 with the help of alkali hydroxide solutions, e.g. sodium hydroxide or potassium hydroxide, or alkali carbonate solutions, e.g. sodium carbonate or potassium carbonate, and then to work up the reaction product in known manner.

As alkali hydroxide or alkali carbonate there are employed aqueous solutions containing 5-50 wt. %, preferably, 30 to 50 wt. % alkali hydroxide. Of the three alkali hydroxides or carbonates the sodium derivative is especially preferred.

The above mentioned pH of 2-6 likewise can be established after the end of the reaction for the production of the peroxycarboxylic acid by addition of corresponding amounts of magnesium hydroxide or oxide, or alkaline earth metal hydroxides, e.g. calcium hydroxide or barium hydroxide, as well as their carbonates, e.g. calcium carbonate, barium carbonate, or earth metal hydroxides, as well as their carbonates, as well as alkali aluminates, e.g. sodium aluminate, potassium aluminate, as well as sodium metaborate. These materials also can be added in dissolved or suspended form, i.e. in aqueous medium.

The phlegmatization agent preferably should be present in an amount of 0.1 to 80 wt. % based on the finished product.

The storage stability is greatly increased by the phlegmatization agent.

In using sodium sulfate which is added either as a solid or in aqueous solution, or is form ed in situ, there also can be used all three possibilities simultaneously, the residual moisture of the peroxycarboxylic acids is reduced after centrifuging about 50%.

This effect occurs especially strongly if the in situ formation of sodium sulfate from the sulfuric acid present in the reaction mixture and the added aqueous sodium hydroxide is carried out at a temperature above the transformation point from sodium sulfate decahydrate to water-free sodium sulfate, i.e. at a temperature beginning at 32.3°-32.4° C.

The process can comprise, consist essentially of, or consist of the stated steps with the materials recited.

Unless otherwise indicated all parts and percentages are by weight.

The invention will be explained in connection with the following examples.

DETAILED DESCRIPTION

Comparison Example

According to the date of the following Example 1, there was reacted an oxidation mixture with dodecanedioic acid (DPDDA) suspended therein.

After a short time the reaction mixture foamed greatly in such a manner that not only did foam form on the liquid surface but also the mixture itself was so strongly permeated with fine gas bubbles that it took up a consistency that culd be characterized as almost cream-like. In this form a handling of the no longer pumpable mixture cannot be considered on an industrial scale.

In contrast by proceeding according to the following Examples 1-8, the formation of foam is suppressed to such an extent that one can work on a large scale without problem.

Also, the partial neutralization of the sulfuric acid following the reaction now can be carried out through ready distribution of the neutralizing agent without any danger of decomposition of active oxygen because of local accumulation of alkali. Furthermore, the suspension of peracid and phlegmatization agent finally obtained is flowable and centrifugable without doing anything further.

EXAMPLE 1

There were dosed into an oxidation mixture consisting of 170 grams of hydrogen peroxide (50 wt. %) and 204 grams of sulfuric acid (96 Wt. %), as well as 1.3 grams of pyridine-2,6-dicarboxylic acid, 115 grams of dodecanedioic acid and the mixture stirred for 8 hours at 50° C. After cooling to 8° C. the mixture was treated at this temperature with 300 grams of sodium sulfate solution (13 wt. %) and subsequently neutralized with 517 grams of sodium hydroxide solution (30 wt. %) until a pH of 3.5 was reached. Subsequently the product was centrifuged and dried.

Drying was at 40° C.

The yield of peracid was: 106.2 grams $\hat{=}$ 81% of theory.

Total AO (active oxygen) content: 3.75%

The dodecanedicarboxylic balance is: 89.9%

|  | 0 Weeks | 4 Weeks | 8 Weeks | 12 Weeks |
|---|---|---|---|---|
| DPDDA-Content | 30.7 | 30.7 | 30.5 | 30.5 |
| AO | 3.75 | 3.75 | 3.73 | 3.73 |

In a similar manner without PDCA addition the DPDDA produced in 12 weeks lost about 10% of its AO content in 12 weeks.

EXAMPLE 2

There were suspended in an oxidation mixture consisting of 102 grams of hydrogen peroxide (50 wt. %), 204 grams of sulfuric acid (96 wt. %) and 25 grams of sodium sulfate solution (13 wt. %), as well as 0.14 gram pyridine-2,6-dicarboxylic acid, 115 grams of dodecanedioic acid and the mixture heated for 8 hours with stirring at 60° C. After cooling to 8° C. the mixture was treated at this temperature with 500 grams of sodium sulfate solution (13 wt. %) and subsequently neutralized with 526 grams of sodium hydroxide solution (30 wt. %) until a pH of 3.5 was reached. Subsequently the mixture was centrifuged and dried.

Drying was at 40° C.

The yield of peracid was: 115 grams $\hat{=}$ 87.7% of theory.

Total AO content: 3.79%

The dodecanedioic acid balance wasd 95.8%

The content of DPDDA was: 31.0%

EXAMPLE 3

There were suspended in an oxidation mixture consisting of 255 grams of hydrogen peroxide (50 wt. %), 510 grams of sulfuric acid (96 wt. %) and 64 grams of sodium sulfate solution (13 wt. %), as well as 0.4 gram pyridine-2,6-dicarboxylic acid, 287.5 grams of dodecanedioic acid and the mixture heated for 8 hours with stirring at 60° C. After cooling to 20° C. the mixture was treated at this temperature with 1 liter of distilled water and filtered with suction. The residue was washed with cold, distilled water and dried.

The yield of peracid was: 303.9 grams≙92.8% of theory.
 Total AO content: 11.64%
 The dodecanedioic acid balance was: 97.0%
 The content of DPDDA was: 95.4%

EXAMPLE 4

There were fed into an oxidation mixture consisting of 102 grams of hydrogen peroxide (50 wt. %), 204 grams of sulfuric acid (96 wt. %) and 25 grams of sodium sulfate solution (13 wt. %), as well as 0.16 gram pyridine-2,6-dicarboxylic acid, 115 grams of dodecanedioic acid and the mixture heated for 6 hours with stirring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and then the mixture was conditioned with 160 grams of sodium sulfate. Subsequently the product was separated and dried at 40° C.

The yield of peracid was: 120.1 grams≙91.5% of theory.
 Total AO content: 4.23%
 The dodecanedioic acid balance was: 99.1%
 The content of DPDDA was: 34.6%

EXAMPLE 5

There were fed into an oxidation mixture consisting of 102 grams of hydrogen peroxide (50 wt. %), 204 grams of sulfuric acid (96 wt. %) and 25 grams of sodium sulfate solution (13 wt. %), as well as 0.8 gram pyridine-2,6-dicarboxylic acid, 115 grams of dodecanedioic acid and the mixture heated for 6 hours with stirring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and the mixture conditioned with 160 grams of sodium sulfate. Subseqently the product was separated and dried.

The yield of peracid was: 118.1 grams≙90.1% of theory.
 Total AO content: 4.49%
 The dodecanedioic acid balance was: 95.6%
 The content of DPDDA was: 36.8%

EXAMPLE 6

There were fed into an oxidation mixture consisting of 102 grams of hydrogen peroxide (50 wt. %), 204 grams of sulfuric acid (96 wt. %) and 25 grams of sodium sulfate solution (13 wt. %), as well as 0.16 gram pyridine-2,6-dicarboxylic acid, 115 grams of dodecanedioic acid and the mixture heated for 4 hours with stirring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and conditioned with 160 grams of solid sodium sulfate. Subseqently the mixture was centrifuged and dried.

The yield of peracid was: 120.2 grams≙91.7% of theory.
 Total AO content: 4.54%
 The dodecanedioic acid balance was: 99.3%
 The content of DPDDA was: 37.1%

EXAMPLE 7

There were fed into an oxidation mixture consisting of 102 grams of hydrogen peroxide (50 wt. %), 204 grams of sulfuric acid (96 wt. %) and 25 grams of sodium sulfate solution (13 wt. %), as well as 0.8 gram pyridine-2,6-dicarboxylic acid, 115 grams of dodecanedioic acid and the mixture heated for 4 hours with stirring at 60° C. After cooling to 40° C. the mixture was treated at this temperature with 526 grams of sodium sulfate solution (30 wt. %) and subsequently neutralized with 523 grams of sodium hydroxide solution (30 wt. %) until a pH of 3.5 was reached and conditioned with 160 grams of sodium sulfate. Subsequently the product was separated and dried.

The yield of peracid was: 119.5 grams≙91.2% of theory.
 Total AO content: 4.42%
 The dodecanedioic acid balance was: 98.5%
 The content of DPDDA was: 36.2%

EXAMPLE 8

There were fed into an oxidation mixture consisting of 127 grams of hydrogen peroxide (40 wt. %), 204 grams of sulfuric acid (96 wt. %), as well as 0.16 gram pyridine-2,6-dicarboxylic acid, 115 grams of dodecanedioic acid and the mixture heated for 4 hours with stirring at 60° C. After cooling to 40° C. the mixture was treated at this temperature with 526 grams of sodium sulfate solution (30 wt. %) and subsequently neutralized with 523 grams of sodium hydroxide solution (30 wt. %) until a pH of 3.5 was reached and conditioned with 160 grams of solid sodium sulfate. Subsequently the mixture was centrifuged and dried.

Drying was at 40° C.

The yield of peracid was: 115.2 grams≙87.8% of theory.
 Total AO content: 4.24%
 The dodecanedioic acid balance was: 95.3%
 The content of DPDDA was: 34.7%

The entire disclosure of German priority application P No. 3418450.3 is hereby incorporated by reference.

EXAMPLE 9

There were fed into an oxidation mixture consisting of 120 grams of hydrogen peroxide (85 wt. %), 306 grams of sulfuric acid (96 wt. %), as well as 0.16 gram pyridine-2,6-dicarboxylic acid, 99,7 grams of isophthalic acid and the mixture heated for 24 hours with stirring at 50° C. After cooling to 8° C. the mixture was treated at this temperature with 300 ml of water. Subsequently the product was separated, washed with distilled cold water and dried.

The yield of peracid was: 91,9 grams≙77,3% of theory.
 Total AO content: 14,37%
 The isophthalic acid balance was: 89,4%
 The content of DPIPA was: 88,4%

EXAMPLE 10

There were fed into an oxidation mixture consisting of 34 grams of hydrogen peroxide (50 wt. %), 66 grams of sulfuric acid (96 wt. %), as well as 0.048 gram pyridine-2,6-dicarboxylic acid, 36,6 grams of brassylic acid and the mixture heated for 6 hours with stirring at 60° C. After cooling to 15° C. the mixture was treated at this temperature with 250 ml of water. Subsequently the product was separated, washed with distilled cold water and dried.

The yield of peracid was: 37,9 grams $\triangleq$ 92,3% of theory.

Total AO content: 11%

The brassylic acid balance was: 95,9%

The content of DPBA was: 95,3%

EXAMPLE 11

There were fed into an oxidation mixture consisting of 102 grams of hydrogen peroxide (50 wt. %), 204 grams of sulfuric acid (96 wt. %) and 25 grams of sodium sulfate solution (13 wt. %), as well als 0.16 gram pyridine-2,6-dicarboxylic acid, 94,1 grams of azelaic acid (techn.) and the mixture heated for 4 hours with stirring at 60° C. After cooling to 20° C. the mixture was treated at this temperature with 500 ml of water. Subsequently the product was separated, washed with distilled cold water and dried.

The yield of peracid was: 91,1 grams

Total AO content: 13,9%

The content of DPAA was: 94,9%

EXAMPLE 12

There were fed into an oxidation mixture consisting of 20,4 grams of hydrogen peroxide (50 wt. %), 30,6 grams of sulfuric acid (96 wt. %) as well as 0,1 gram pyridine-2,6 dicarboxylic acid, 34 grams of decane carboxylic acid and the mixture heated for 3 hours with stirring at 35° C. After cooling to 20° C. the mixture was treated at this temperature with 50 ml of water. Subsequently the product was separated, washed with distilled cold water and dried.

The yield of peracid was: 33,9 g=90,2% of theory

Total AO-content: 7,85%

The decane carboxylic acid balance was: 99,9%

The content of PDA was: 91,2%

What is claimed is:

1. A process for the suppression of foam in peroxycarboxylic acid forming reactions comprising carrying out the peroxidation reaction of the carboxylic acid in the presence of a foam suppression agent, wherein said peroxidation reaction comprises reacting a carboxylic acid selected from aliphatic carboxylic acids having from 6 to 16 carbons and aromatic carboxylic acids having 7 to 9 carbons, with a peroxidation mixture comprising a mixture of $H_2O_2$, $H_2O$ and $H_2SO_4$, and wherein said foam suppression agent is 2,6-pyridine dicarboxylic acid, shown in the formula below:

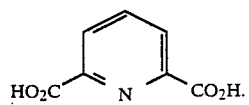

and said foam suppression agent is present in the amount 0.35 to 1.6 wt % relative to the amount of $H_2O_2$ present.

2. A process according to claim 1 wherein the acid is an alkanoic acid, alkandioic acid, or benzene carboxylic acid.

3. A process according to claim 1 wherein the reaction is carried out with a molar ratio of hydrogen peroxide to carboxylic acid of 1 to 10:1.

4. A process according to claim 1 wherein the sulfuric acid and carboxylic acid are employed in the molar ratio of 1 to 10:1.

5. A process according to claim 1 wherein the reaction is carried out at a temperature of 35° to 60° C., the reaction mixture is then cooled to a lower temperature of 45° to 5° C. and treated with an aqueous alkali metal sulfate solution and the mixture is then adjusted to pH 2 to 6 with aqueous alkali metal hydroxide or alkali metal carbonate solution.

* * * * *

UNITED STATES PATENT AND TRADEMARK OFFICE
CERTIFICATE OF CORRECTION

PATENT NO. : 4,959,497

DATED : September 25, 1990

INVENTOR(S) : DANKOWSKI, Manfred

It is certified that error appears in the above-identified patent and that said Letters Patent is hereby corrected as shown below:

On the title page, change "[73] Assignee: Degussa Akteingesellschaft, Frankfurt am Main, Fed. Rep. of Germany" to --[73] Assignees: Degussa Akteingesellschaft, Frankfurt am Main, Fed. Rep. of Germany; and Kenkel KGAA, Dusseldorf, Fed. Rep. of Germany--.

Signed and Sealed this

Sixth Day of October, 1992

Attest:

DOUGLAS B. COMER

Attesting Officer

Acting Commissioner of Patents and Trademarks